US008642930B2

(12) United States Patent
Kraus et al.

(10) Patent No.: US 8,642,930 B2
(45) Date of Patent: Feb. 4, 2014

(54) DEVICE FOR HEATING AN OBJECT BY MEANS OF A WATER BATH

(75) Inventors: Steffen Kraus, Wiesloch (DE); Erwin Schneider, Nussloch (DE)

(73) Assignee: pfm medical ag, Cologne (DE)

( * ) Notice: Subject to any disclaimer, the term of this patent is extended or adjusted under 35 U.S.C. 154(b) by 425 days.

(21) Appl. No.: 12/988,728

(22) PCT Filed: Apr. 20, 2009

(86) PCT No.: PCT/DE2009/000504
§ 371 (c)(1),
(2), (4) Date: Oct. 29, 2010

(87) PCT Pub. No.: WO2009/129777
PCT Pub. Date: Oct. 29, 2009

(65) Prior Publication Data

US 2011/0031232 A1 Feb. 10, 2011

(30) Foreign Application Priority Data

Apr. 21, 2008 (DE) ........................ 10 2008 020 002
May 15, 2008 (DE) ........................ 10 2008 023 660

(51) Int. Cl.
*G01N 33/00* (2006.01)
*G01N 33/48* (2006.01)
*G01N 33/483* (2006.01)
*F27D 11/00* (2006.01)

(52) U.S. Cl.
USPC .......... 219/438; 219/439; 219/441; 422/68.1; 422/536

(58) Field of Classification Search
None
See application file for complete search history.

(56) References Cited

U.S. PATENT DOCUMENTS 2,428,996 A * 10/1947 Schworm, Jr. ................ 219/428
2,533,964 A * 12/1950 Scherer ......................... 422/285
2,653,214 A 9/1953 Shaw
2,813,189 A 11/1957 Lawler
3,818,818 A * 6/1974 Hice, Sr. ......................... 99/330
3,985,511 A * 10/1976 Betts ............................. 422/561
D275,033 S * 8/1984 Postlewait ................... D24/217
D288,600 S * 3/1987 Vander Hout et al. ....... D24/217
4,782,835 A * 11/1988 Bernardini .................... 607/114

(Continued)

FOREIGN PATENT DOCUMENTS

DE 865 392 2/1953
DE 908 672 4/1954

(Continued)

OTHER PUBLICATIONS

International Search Report and Written Opinion for International Application No. PCT/DE2009/000504, mailed Aug. 30, 2011.

(Continued)

*Primary Examiner* — Joseph M Pelham
(74) *Attorney, Agent, or Firm* — Alston & Bird LLP

(57) ABSTRACT

The invention relates to a device for heating an object by means of a water bath, in particular for strips of pathological or histological sections, before a microscopic examination, comprising a housing (1) and a trough (2) inserted in the housing (1), wherein the water bath is heated by means of an electrical heater, characterized in that the electrical heater comprises at least one hotplate (4) provided on the base (3) of the trough (2).

32 Claims, 2 Drawing Sheets

(56) References Cited

U.S. PATENT DOCUMENTS

| | | | | | |
|---|---|---|---|---|---|
| D309,013 | S | * | 7/1990 | Vander Hout | D24/217 |
| 4,967,061 | A | | 10/1990 | Weber, Jr. et al. | |
| 5,017,758 | A | * | 5/1991 | Kirkman et al. | 219/205 |
| 5,168,959 | A | * | 12/1992 | Davis | 184/1.5 |
| 5,520,884 | A | | 5/1996 | Croucher | |
| 5,687,635 | A | * | 11/1997 | Stockton | 9/281 |
| 6,087,636 | A | * | 7/2000 | Faries et al. | 219/429 |
| 6,091,058 | A | * | 7/2000 | Faries et al. | 219/430 |
| 6,131,563 | A | * | 10/2000 | Bonnetin et al. | 126/373.1 |
| 6,184,500 | B1 | * | 2/2001 | Glucksman | 219/432 |
| 6,264,895 | B1 | * | 7/2001 | Johnson | 422/530 |
| 6,301,961 | B1 | * | 10/2001 | Rolfes et al. | 73/328 |
| 6,303,910 | B2 | * | 10/2001 | Glucksman et al. | 219/430 |
| 6,417,495 | B1 | * | 7/2002 | Glucksman | 219/432 |
| 6,756,015 | B2 | * | 6/2004 | Dalkidis et al. | 422/68.1 |
| 6,756,567 | B1 | * | 6/2004 | Suen | 219/424 |
| 6,884,970 | B2 | * | 4/2005 | Lehman | 219/432 |
| 6,927,365 | B2 | * | 8/2005 | Li | 219/432 |
| 7,959,860 | B2 | * | 6/2011 | Faries et al. | 422/62 |
| 8,148,666 | B2 | * | 4/2012 | Faries et al. | 219/429 |
| 2002/0025276 | A1 | * | 2/2002 | Dalkidis et al. | 422/68.1 |
| 2003/0132216 | A1 | * | 7/2003 | Li | 219/432 |
| 2004/0208780 | A1 | * | 10/2004 | Faries et al. | 422/3 |
| 2004/0258567 | A1 | * | 12/2004 | Kokin et al. | 422/68.1 |
| 2006/0201938 | A1 | * | 9/2006 | Wojcik et al. | 219/761 |
| 2007/0110634 | A1 | * | 5/2007 | Heimberg et al. | 422/102 |
| 2008/0023462 | A1 | * | 1/2008 | Shei et al. | 219/394 |
| 2008/0142502 | A1 | * | 6/2008 | Bratcher et al. | 219/450.1 |
| 2011/0203570 | A1 | * | 8/2011 | Popeil et al. | 126/369 |

FOREIGN PATENT DOCUMENTS

| | | | | |
|---|---|---|---|---|
| DE | 42 39 232 | | | 5/1994 |
| DE | 203 01 789 | | | 4/2003 |
| DE | 20 2005 015 2 | | | 1/2006 |
| GB | 2 226 161 | | | 6/1990 |
| JP | 2008177063 | A | * | 7/2008 |
| SU | 1648386 | A | * | 5/1991 |
| WO | WO 90/05329 | A1 | | 5/1990 |
| WO | WO 01/68014 | A1 | | 9/2001 |

OTHER PUBLICATIONS

Translation of the Written Opinion for International Application No. PCT/DE2009/000504, filed Apr. 20, 2009.

* cited by examiner

DEVICE FOR HEATING AN OBJECT BY MEANS OF A WATER BATH

BACKGROUND OF THE INVENTION

1. Field of the Invention

The invention concerns a device for heating an object by means of a water bath, especially for strips of pathologic or histologic sections, especially paraffin sections, before microscopic examination, with a housing and a trough inserted in the housing, the water bath being temperature-controllable by means of electric heating.

2. Description of Related Art

Generic devices are known from practice in a variety of versions. They are used to heat or temperature-control a water bath, this again being used for strips of paraffin sections in the histologic laboratory.

The devices known from practice of the generic type are problematical to the extent that the desired temperature can only be approximately stipulated via multistage switches. Not rarely, the temperature is measured via an external thermometer or no temperature display at all is provided. The known devices are therefore problematical in use and have only limited operating convenience.

The underlying task of the present invention is therefore to configure and modify a device for heating of an object with a water bath, especially the strips of pathologic and histologic sections, especially paraffin sections, before microscopic examination, so that the highest degree of operational reliability with sufficiently good operating convenience is achieved in the simplest design.

SUMMARY OF VARIOUS EMBODIMENTS

The aforementioned task is solved by the various embodiments of the present invention described herein. The generic device is characterized by the fact that electric heating includes at least one heating plate allocated to the bottom of the trough, and that a stipulated water temperature is controllable.

According to the invention, electric heating includes at least one heating plate assigned to the bottom of the trough. The trough bottom is therefore directly heated over its surface. A stipulated water temperature can be controlled according to the heating plate. This means that, throughout operation, the water temperature is determined by means of a temperature sensor and heating regulated accordingly. It is therefore guaranteed that the water bath always has the desired temperature, regardless of the ambient temperature, the through-put and the operating time.

The electric heating advantageously includes at least two or more heating plates, in which case the bottom area of the trough can be sectioned accordingly. The heating plates can then be activated together or individually. It is also conceivable that the heating plates include a circular configuration and circular ring segments around it in the center of the bottom area. Here again, joint or individual activation is possible according to the energy demand.

In principle, it is conceivable that the heating plates, regardless of their specific configuration, can be integral components of the bottom of the trough. It is advantageous, with respect to simple design, if the heating plates are connected, preferably glued, from the bottom to the bottom of the trough. It is then a particularly advantageous, if the heating plates are glued with an adhesive with high heat conductivity, in order to favor heat conduction into the water being heated.

It is also conceivable that the side walls of the trough are provided with heat elements, in which these heat elements can also be heating plates, but also heating tubes, heating cables, etc.

Heating of the water bath is favored by the fact that the wall of the trough in the bottom area is made as thin as possible, preferably has a thickness of about 1 mm. In other words, the bottom area should be made thin enough, that it is still sufficiently stable, but guarantees excellent heat transfer from the heating device or heating element into the water.

With reference to configuration or manufacture of the housing, it is conceivable that it is made as a monolithic block. The housing can then be made from an aluminum block. The surface of the housing is preferably brightly anodized.

The trough arranged in the housing and fastened there can be made from aluminum. The surface of the trough can also be anodized, in which case the thing to do is to darkly anodize the surface of the trough, especially make it black, in order to avoid reflections within the trough.

With particular advantage, the trough has a support surface for positioning of samples, slides, etc. at least partially covering the trough. It is then conceivable that the support surface covers the entire trough. The support surface can have significant width, namely a width in the range from 30 mm to 70 mm, preferably about 50 mm. The precaution of the support surface offers the operating person significant safety and facilitation during work.

To further advantage, the support surface is bounded by a continuous outer edge raised relative to the support surface, so that no liquid can reach the base or table.

It is also conceivable that the support or edge has a marking for the position of a discharge/drain, namely as an orientation for the operating person.

The support surface can also be heated. Heating of the support surface can be activated and controlled independently of heating in the bottom area. In each case, it is essential that the support surface can also serve for temperature control or drying of objects situated on it.

The housing and/or the trough can be equipped with additional functional devices or units. For example, it is conceivable that the trough is equipped with an optical and/or electrical or electronic water level display. An optical water level display could be implemented via a window in the trough, visible from outside of the housing. An electrical or electronic water level display could be implemented via a display on the housing.

A further advantage is, if the trough is equipped with illumination that could be activated in alternation, preferably with underwater illumination. Illumination includes at least one diode as illuminator. The illumination advantageously includes two diodes, switchable independently of each other, preferably for emission of white and blue light. In principle, it is conceivable that the illumination is designed as RGB illumination with adjustable colors or adjustable wavelength. The illumination is preferably made in the sides of the trough, so that dazzling of the operating person is effectively avoided.

It has already been mentioned that the housing can be equipped with a display. The housing could have a front viewing surface with a display and with separate or integrated operating elements. If the operating elements are integrated in the display, the display with the operating elements could be designed with a touch panel.

Electronics for temperature control and control of additional parameters or quantities can also be provided in the housing. It goes without saying that the electronics receive signals from sensor devices or a transmitter arranged in the wall of the trough or provided there. In each case, the temperature is regulated to a stipulated or adjustable value, regardless of external influences.

Also advantageously, the electronics include an emergency off function, so that heating is deactivated on falling below a preferably stipulated lower water level in the trough. It is also conceivable that during falling short of a lower water level, an optical and/or acoustic signal occurs, according to which refilling with water is necessary. It is also conceivable that the device is provided with a water connection, which automatically controls the water level. In this case, the filling amount is detected and can be continuously replenished.

With reference to assembly of the devices, it is advantageous, if the trough is inserted into the housing and fastened there. The thing to do is to insert the trough from above into the housing, in which case the housing includes an inner edge that serves for support. For reliable assembly, the trough is preferably screwed to the housing from below. No fastening devices are recognizable from above the device in the context of this configuration.

Finally, a bottom cover for closure of the housing on the bottom is provided, in which the bottom cover is screwed to the housing. Support pads for secure setup of the device are preferably provided on the screws.

BRIEF DESCRIPTION OF THE SEVERAL VIEWS OF THE DRAWINGS

There are different possibilities for configuring and modifying the instructions of the present invention advantageously. For this purpose, various additional embodiments, on the one hand, and the following explanation of the practical example of the invention with reference to the drawing, on the other hand, are referred to. In conjunction with explanation of the preferred practical example of the invention with reference to the drawing, generally preferred embodiments and modifications of the instructions are also explained. In the drawing

DETAILED DESCRIPTION

Figure 1:
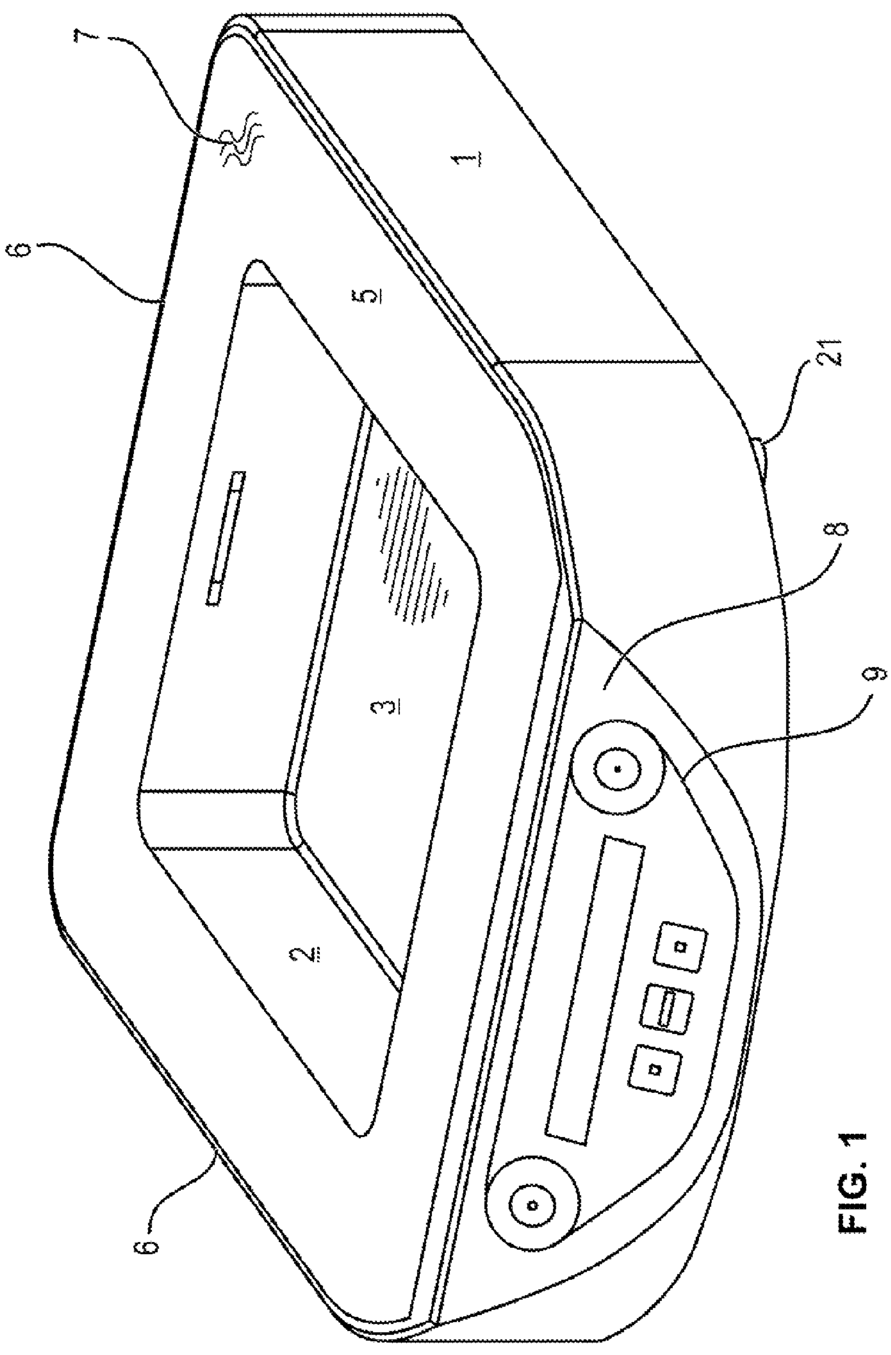
FIG. 1 shows a schematic view of a practical example of the device according to the invention and FIG. 2 shows the object from FIG. 1 with the essential components in an exploded view.

FIG. 1 schematically depicts a practical example of a device according to the invention for heating of an object with a water bath, namely a device for heating of paraffin sections in a pathologic/histologic laboratory. The device includes a housing 1 and a trough 2 inserted into the housing 1. The water bath can be temperature-controlled with electric heating.

Figure 2:
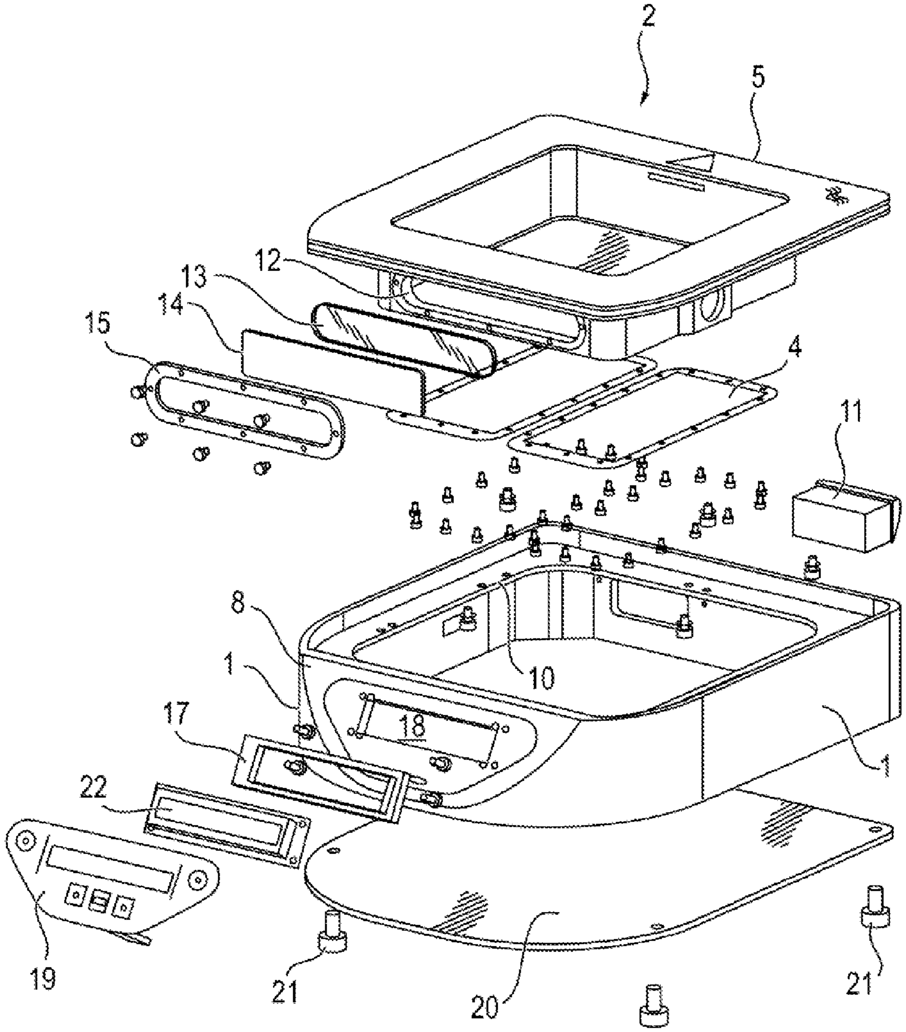

Electric heating according to the invention includes at least one heating plate 4 assigned to the bottom 3 of trough 2, the heating plate only being indicated in FIG. 2. A stipulated water temperature can be controlled with the electric heating.

According to the depiction in FIG. 2, two heating plates 4, independent of each other, are provided. The two heating plates 4 can be activated in alternation, together or individually. They are glued from the bottom to the bottom 3 of trough 2, specifically with an adhesive with high heat conductivity.

It should be noted here that the wall of trough 2 in the bottom area is made as thin as possible, preferably with a thickness in the range from 1 mm or even less.

The housing 1 is made as a monolithic block from an aluminum block. The surface of the housing 1 is brightly anodized.

The trough 2 is also made of aluminum and anodized darkly or black.

FIG. 1 also shows that the trough 2 is equipped with a continuous support surface 5 that serves to support samples, sample holders, etc. The support surface 5 is heated. It has a width of about 50 mm.

In additional, an edge 6 surrounding the support surface 5 is also provided, which secures parts against falling down, on the one hand, and, on the other hand, prevents liquid from running down laterally along the housing wall. Soiling is thus avoided and a high degree of operational reliability is achieved.

The support surface 5 also has a marking 7 for the position of a discharge/drain. The drain can be arranged in trough 2 or in housing 1, discharge can occur into trough 2 or into a discharge vessel, not shown in the figures, arranged in housing 1.

FIG. 1 also shows that in the front area of the device, a display 9 is provided as touch panel in a sloped surface 8. The display 9 therefore includes a display device and operating elements. Water temperatures can be stipulated via the touch panel and a program can also be activated via an internal processor up to automatic switching off of the device.

FIG. 2 shows essential parts of the device according to the invention in an exploded view. The housing 1 has an inner edge 10 for insertion or positioning of trough 2, in which the trough 2 is screwed to housing 1 from the bottom. Two heating plates 4 are also provided, which are glued from the bottom to the bottom 3 of trough 2 with a special glue, namely with a glue with high heat conductivity.

In the interest of simple depiction, showing of the electronics is dispensed with. It is only indicated in FIG. 2 that an instrument socket 11 for electrical connection of the device is provided. From there, the entire electrical/electronic system is supplied with current, this having no significance according to the invention.

A recess 12 is provided in trough 2, which is closed via a glass insert 13, a seal 14 and a glass cover 15. This precaution permits visual control of the water level, this occurring via a view window 16 in display 9 or on display 9. The display 9 is fastened in a recess 18 in the housing via a frame 17, the display 9 being covered by a special film 19.

FIG. 2 also shows that housing 1 is closed from the bottom with a bottom plate 20, support pads 21 being provided for secure standing on the bottom.

Finally, it is noted that the practical example just explained serves merely to explain the device according to the invention, but does not restrict it to the practical example.

The invention claimed is:

1. A device for heating strips of pathologic and histologic sections with a water bath before microscopic examination, said device comprising:

a housing and a basin inserted in the housing, the water bath being temperature-controlled by means of electric heating, wherein the electric heating includes at least one heating plate located proximate a bottom of the basin, and wherein a stipulated water temperature can be controlled, wherein the basin has a support surface at least partially enclosing the basin for positioning of samples, wherein the support surface is heated, and wherein heating of the support surface is activatable and controllable independently of heating of a bottom area.

2. The device according to claim 1, wherein the electric heating includes at least two or more heating plates.

3. The device according to claim 2, wherein the heating plates can be activated together.

4. The device according to claim 1, wherein the heating plate comprises the bottom of the basin.

5. The device according to claim 1, wherein the heating plate is connected to the bottom of the basin or to the basin from the bottom.

6. The device according to claim 5, wherein the heating plate is glued with an adhesive with high heat conductivity.

7. The device according to claim 1, wherein side walls of the basin are provided with heating elements.

8. The device according to claim 7, wherein the heating elements are heating plates, heating tubes or heating cables.

9. The device according to claim 1, wherein a wall of the basin is made with a thickness in the range of about 1 mm in a bottom area.

10. The device according to claim 1, wherein the housing is made as a monolithic block.

11. The device according to claim 10, wherein the housing is made from an aluminum block.

12. The device according to claim 11, wherein a surface of the housing is brightly anodized.

13. The device according to claim 1, wherein the basin is made from aluminum.

14. The device according to claim 13, wherein a surface of the basin is darkly anodized.

15. The device according to claim 1, wherein the support surface completely encloses the basin.

16. The device according to claim 1, wherein the support surface has a width in the range from 30 mm to 70 mm.

17. The device according to claim 1, wherein the support surface is bounded by a continuous outer edge, raised relative to the support surface.

18. The device according to claim 17, wherein the support surface or the outer edge has a marking for the position of a discharge/drain.

19. The device according to claim 1, wherein the basin is equipped with an optical and/or electric or electronic water level display.

20. The device according to claim 1, wherein the housing has a front view surface with a display and operating elements.

21. The device according to claim 20, wherein the operating elements are integrated in the display, and wherein the display is designed as a touch panel.

22. The device according to claim 1, wherein electronics for temperature control are provided in the housing.

23. The device according to claim 22, wherein the temperature control is laid out, so that the water bath has reached a set operating temperature in the range from 40° C. to 45° C., already after about 2 to 5 minutes in which case individual adjustment and/or change of the operating temperature is possible.

24. The device according to claim 22, wherein the electronics includes an emergency off function, which deactivates heating on falling below a stipulated lower water level in the.

25. The device according to claim 1, wherein the basin is inserted into the housing and fastened there.

26. The device according to claim 25, wherein the basin is screwed to the housing from the bottom.

27. The device according to claim 1, wherein a bottom cover to close the housing on the bottom is provided.

28. The device according to claim 1, wherein the basin is equipped with alternately activatable illumination with underwater illumination.

29. The device according to claim 28, wherein the illumination includes at least one diode as an illumination device.

30. The device according to claim 28, wherein illumination includes two diodes, switchable independently from each other.

31. The device according to claim 28, wherein illumination is designed as RGB illumination with adjustable colors or adjustable wavelength.

32. The device according to claim 28, wherein illumination is performed in sides of the basin.

* * * * *

UNITED STATES PATENT AND TRADEMARK OFFICE

CERTIFICATE OF CORRECTION

PATENT NO. : 8,642,930 B2
APPLICATION NO. : 12/988728
DATED : February 4, 2014
INVENTOR(S) : Kraus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 433 days.

Signed and Sealed this
Twenty-ninth Day of September, 2015

Michelle K. Lee
*Director of the United States Patent and Trademark Office*